United States Patent [19]

Paparozzi

[11] Patent Number: Plant 6,749

[45] Date of Patent: Apr. 25, 1989

[54] CONCETTA TM (PAPCONC) C.V. (ROSE PLANT)

[75] Inventor: Ellen T. Paparozzi, Lincoln, Nebr.

[73] Assignee: The Board of Regents of the University of Nebraska, Lincoln, Nebr.

[21] Appl. No.: 100,777

[22] Filed: Sep. 24, 1987

[51] Int. Cl.[4] ..... A01H 5/00

[52] U.S. Cl. ..... Plt./20

[58] Field of Search ..... Plt. 20, 28

*Primary Examiner*—Robert E. Bagwill

*Attorney, Agent, or Firm*—Vincent L. Carney

[57] ABSTRACT

A new and distinct variety of rose plant of the hybrid tea rose class, which was originated as a sport of the rose Gabriella; characterized by its bright orange red, well-formed hybrid tea type blooms with dark velvet overtones on the outer edges of the open flower; disease resistant with everblooming habit and outstanding pot forcing characteristics.

1 Drawing Sheet

The present invention relates to a new and distinct variety of rose plant of the hybrid tea rose class, which was originated as a sport of the rose, Gabriella.

The new variety resulted from a single plant included in a research program. Asexual propagation of the sport has been achieved by both rooted cuttings and tissue culture.

This new variety is distinguished from its parent only by its unusual color and the long-lasting habit of its blooms.

Among the novel characteristics possessed by this new variety which distinguishes it from all other varieties of which I am aware are:

1. Its upright habit of growth, forming a dense shrub that grows vigorously on its own root system. Flowers arise singly or doubly (rarely in clusters) on long stems from a perfectly formed bud, making excellent cut flowers.

2. The general color tonality of the flower is a hot orange, becoming slightly burnished on the edge of the petals with aging.

3. The flower has a lasting quality that is unique to the extent that as the large number of petals slowly open and curl back, the color and texture of the bloom shows no fading over an unusual length of time. The waxy, adherent petals remain on the flower after it fades. The dried flower changes color to a bright red, but still appears fresh.

4. In addition to being an excellent greenhouse cut flower rose, this plant has proven "winter hardy" outdoors.

Asexual reproduction by tissue culture and cuttings of the new variety in Salt Lake County, Utah, shows that the foregoing and other distinguishing characteristics come true to form and are established and transmitted through succeeding propagations.

The new and improved rose variety which I discovered is an unusually vigorous hybrid tea rose with an unusual hot orange flower that keeps its color and substance for an extended period of time. The flowers, about two inches across, are complemented by a fresh fruity fragrance that is especially strong at different parts of the day.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Pantone Color Formula Guide (PMS), 18th Edition, 1985–1986. The terminology used in color description herein refers to plate numbers in the aforementioned color chart, e.g., "357" is sample color 357 in the Pantone Color Formula Guide.

The following observations are made of specimens grown under glass at the East Campus, University of Nebraska, Lincoln, Nebr., and indoors at Salt Lake County, Utah, during the month of January.

FLOWER

Blooming habit: Recurrent and continuous.

A. Bud:

(1) *Size.*—Small.

(2) *Form.*—Urn-shaped as it begins opening.

(3) *Color.*—When sepals first divide: Pantone 171. When petals begin to unfurl: Pantone 172. When half-bloom: Pantone Warm Red on inside of petals with Pantone 170 on reverse side of petals.

(4) *Sepals.*—Usually two with thin white entire margins extending beyond the bud in early bud development becoming shorter than petals as bud unfurls; usually three with stipulate margins stipules becoming reduced with bud opening.

(5) *Peduncle.*—Length 2–3". Aspect — upper smooth, lower inch with some prickles. Strength — medium erect. Color — PMS 377.

B. Bloom:

(1) *Size.*—2–2½".

(2) *Borne.*—Singly.

(3) *Form.*—Urn-shaped at first, becoming high-centered as petals curl outward, becoming ruffled and reflexed at maturity.

(4) *Petalage.*—30.

(5) *Color.*—During first two days. Center of Flower — near PMS 172. Outer petals — PMS Warm Red. Base of petals: near PMS 108. Reverse of petals — PMS 170.

(6) *Color change.*—As bloom ages, near PMS 179 with a slight overlay of PMS 180. General tonality, deep coral orange changing to a warm red with dark overtones on the edge of the petals.

Color is very stable and uniform and retains good color after three or more days.

C. Petals:
(1) *Texture.*—Thick, leathery.
(2) *Appearance.*—Velvety on inside, smooth on outside.
(3) *Form.*—Rounded and reflexed.
(4) *Arrangement.*—Imbricated.
(5) *Petaloids in center.*—Very few.
(6) *Persistence.*—Persist.
(7) *Fragrance.*—Medium fruity.
(8) Lasting quality.—Exceptionally long on the plant or as cut flower.

REPRODUCTIVE ORGANS

A. Stamens, anthers: Regularly arranged around styles.
(1) *Color.*—PMS 109.
B. Pollen: PMS 108.
C. Styles: In bunches, uneven length, short, thin and reddish just below styles.
D. Stigmas:
*Color.*—127.
E. Hips: None observed.

PLANT

A. Form: Upright and compact.
B. Growth: Very vigorous and uniform branching.
*Height attained.*—2 to 3 feet at maturity.
C. Foliage: Compound, 5 to 7 leaflets.
(2) *Size.*—Medium.
(2) *Quantity.*—Abundant.
(3) *Color.*—New foliage: upper side — PMS 357, under side — PMS 195. Old foliage: upper side — PMS 357, under side — PMC 371.
(4) *Shape.*—Oval, pointed.

(5) *Texture.*—Upper side — leathery. Under side — smooth except for venation.
(6) *Edge.*—Serrated.
(7) *Serration.*—Finely biserrate.
(8) *Leaf stem.*—Color — PMS 357; under side — PMS 370.
(9) *Stipules.*—Medium, slightly bearded.
D. Wood:
(1) *New wood.*—Color — PMS 370. Bark — smooth.
(2) *Old wood.*—Color — PMS 371. Bark — smooth to slightly furrowed.
E. Thorns:
(1) *Thorns.*—Quantity: on main stalks from base — none; on laterals from stalk — few. Form: flat base. Length: small. Color when young — PMS 190. Position: irregular.
(2) *Prickles.*—Quantity: On main stalks — none; on laterals — few to none.
F. Plant's disease resistance:
(1) *Mildew.*—Good resistance under normal spray program.
(2) *Blackspot.*—Good resistance under normal spray program.
(3) *Rust.*—None observed.
G. Winter hardiness: Good winter hardiness.

I claim:

1. A new and distinct variety of rose plant of the hybrid tea rose class, substantially as shown and described, characterized particularly by its brilliant orange red color with a darker velvety overtone to its open flowers; plant growth somewhat similar to that of its parent, Gabriella, but more adaptable to pot forcing and growing outdoors even in cold climates.

* * * * *

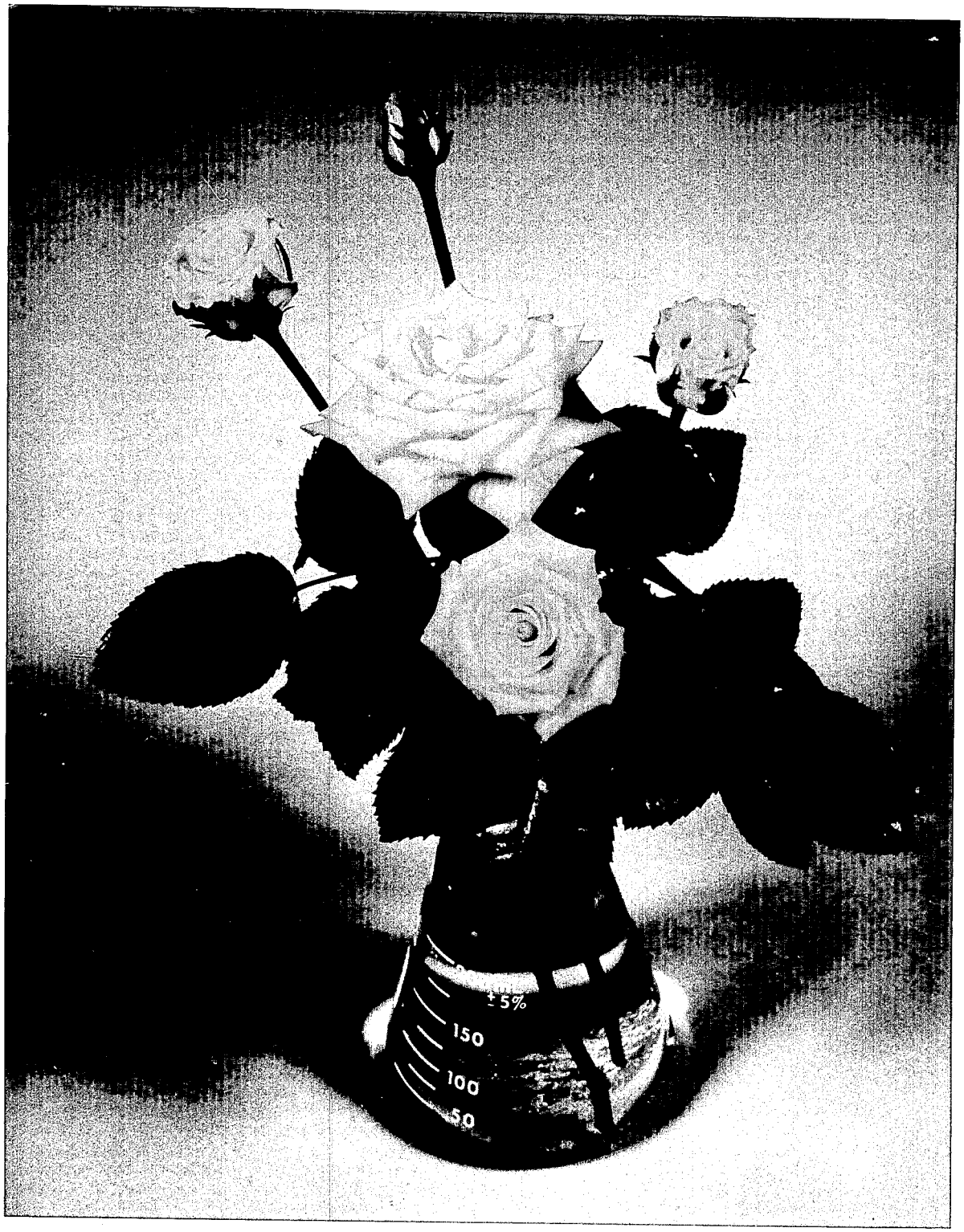
±5%
150
100
50